Figure 1A:
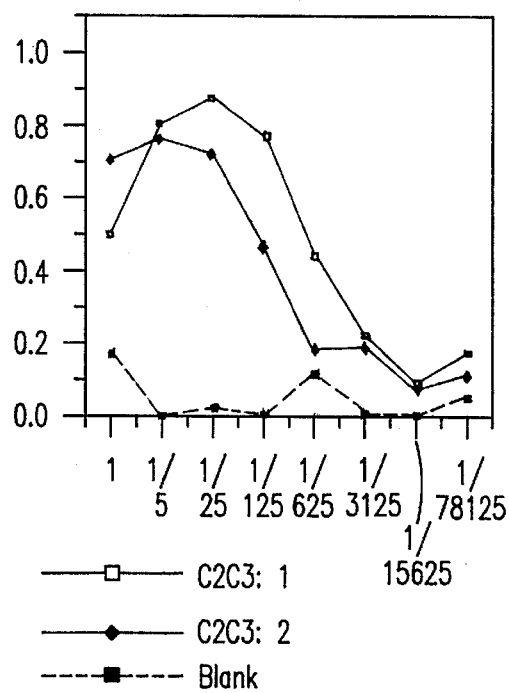
Figure 1A:
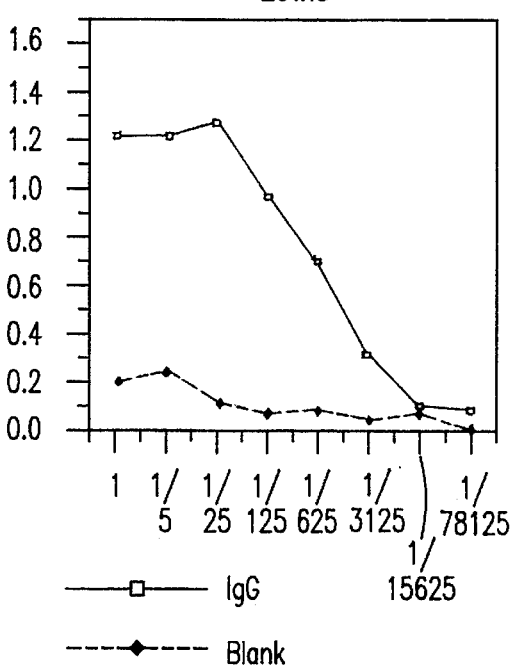
Figure 1A:
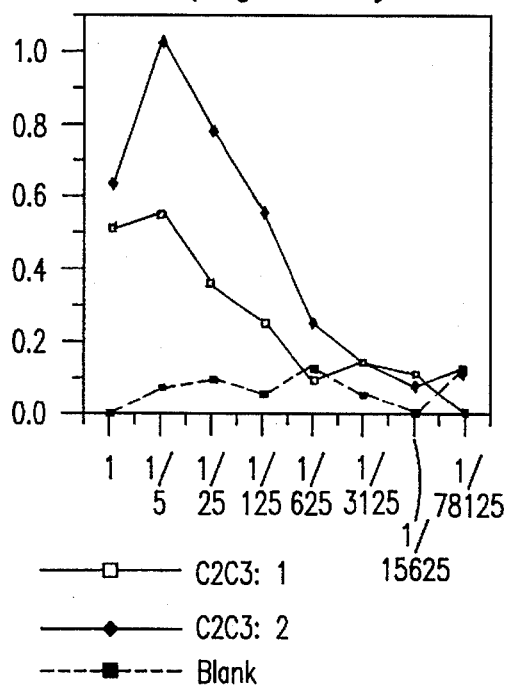
Figure 1A:
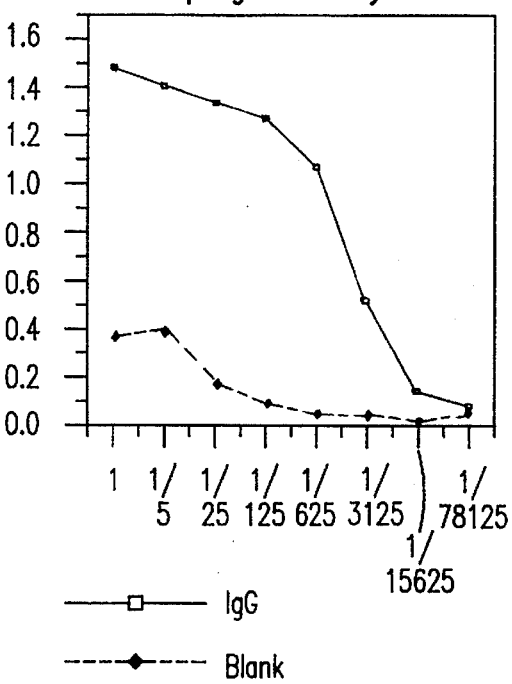
Figure 1B:
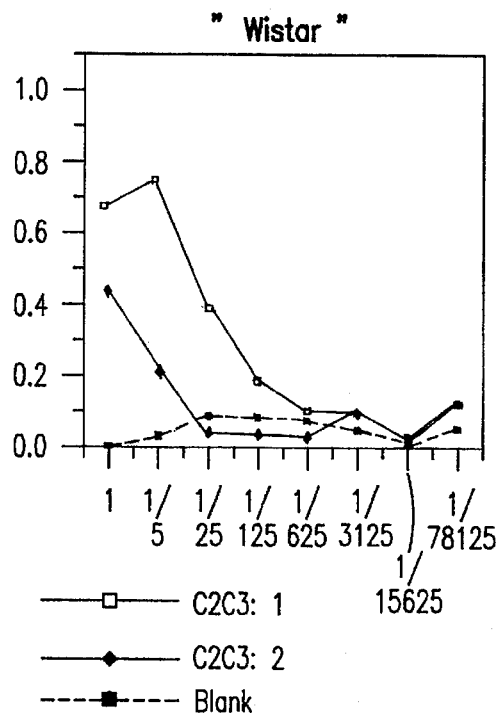
Figure 1B:
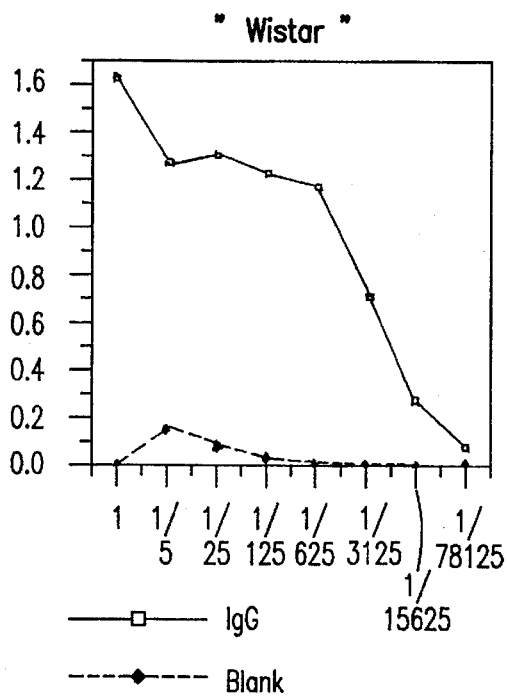
Figure 1B:
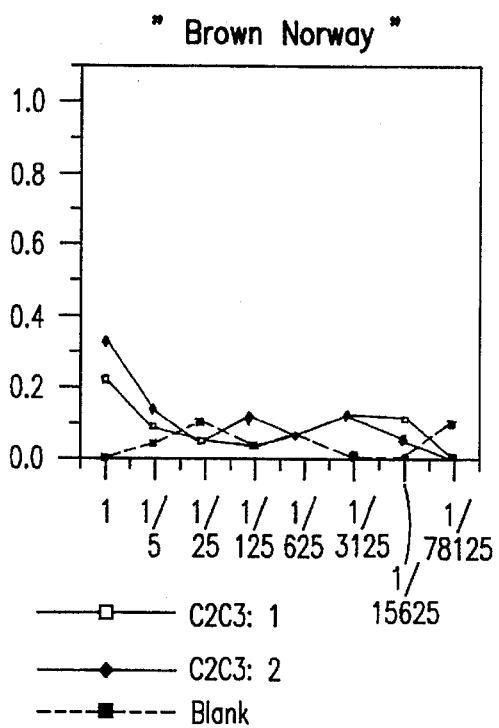
Figure 1B:
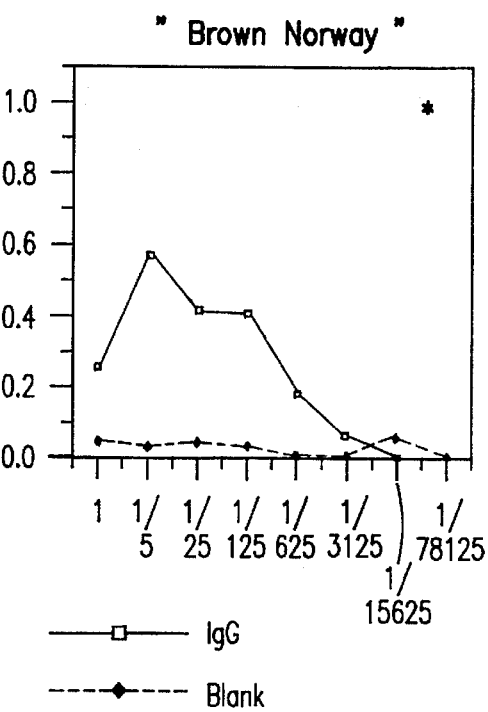

United States Patent [19]

Hellman

[11] Patent Number: 5,653,980
[45] Date of Patent: Aug. 5, 1997

[54] VACCINE COMPRISING PART OF CONSTANT REGION OF IGE FOR TREATMENT OF IGE-MEDIATED ALLERGIC REACTIONS

[76] Inventor: Lars T. Hellman, Väderkvarnsgatan 11A, S-753 29 Uppsala, Sweden

[21] Appl. No.: 196,227

[22] PCT Filed: Sep. 25, 1992

[86] PCT No.: PCT/SE92/00673

§ 371 Date: Mar. 23, 1994

§ 102(e) Date: Mar. 23, 1994

[87] PCT Pub. No.: WO93/05810

PCT Pub. Date: Apr. 1, 1993

[30] Foreign Application Priority Data

Sep. 26, 1991 [SE] Sweden .................................. 9102808

[51] Int. Cl.$^6$ .................. A61K 39/44; A61K 39/385; A61K 39/395; C12P 21/08
[52] U.S. Cl. .................. 424/184.1; 424/192.1; 424/193.1; 424/200.1; 424/800; 424/801; 424/805; 424/809; 424/810; 514/2; 514/12; 530/391.1; 530/862; 530/867; 530/876; 530/868; 536/53
[58] Field of Search .................. 530/371.1, 388.23, 530/391.1; 424/133.1, 134.1, 143.1, 141.1, 178.1, 184.1, 193.1, 192.1, 200.1; 514/2

[56] References Cited

FOREIGN PATENT DOCUMENTS

| 0 396 505 | 11/1990 | European Pat. Off. |
| 0 403 312 | 12/1990 | European Pat. Off. |
| WO-A-89/04834 | 6/1989 | WIPO |
| 8906138 | 7/1989 | WIPO |

OTHER PUBLICATIONS

Burt et al.; "Analysis of the Interaction Between Rat Immunoglobulin E and Rat Mast Cells Using Anti-Peptide Antibodies"; Mol. Immunol.; Apr. 1987, 24 (4), pp. 379-389.
Gould et al.; "Recombinant Human IgE"; Int. Arch Allergy Appl. Immunol, 1987, 82 (3-4); pp. 392-393.
Baniyash et al.; "Inhibition of IgE Binding to Mast Cells and Basophils by Monoclonal Antibodies to Murine IgE"; Eur. J. Immunol, 1984, Sep.; 14(9); pp. 799-807.
Spiegelberg, HL et al (1987) J. Clin. Lab. Anal. 1:251-261.
Dlukthun, Biotechnology 9:545-551, 1991.
Helm et al., Nature 331: 180-183, 1988.
Helm et al., PNAS 86:9465-9469, 1989.
Vercelli et al., Nature 338:649-651, 1989.
Smith et al., Gene 67: 31-40 1988.
Stanworth et al., The Lancet 336:1279-1281, 1990.
Abaza et al. J. Protein Chemistry 11;433-444, 1992.
Devlin, "Textbook of Biochemistry with Clinical Correlations" 2nd Ed., 1980, John Wiley & Sons, p. 49.

*Primary Examiner*—Lila Feisee
*Assistant Examiner*—John Lucas
*Attorney, Agent, or Firm*—Bacon & Thomas

[57] ABSTRACT

The invention relates to a vaccine, preferably for human use, against IgE-mediated allergic reactions. The vaccine contains a protein having the entire amino acid sequence of the constant CH2-CH3 domains of the epsilon chain of the IgE molecule or a structurally stable unit of said amino acid sequence, the protein optionally being coupled to one or more heterologous carrier proteins, and optionally containing an adjuvant. The vaccine is injected, with or without adjuvant, to raise the concentration of endogenous anti-IgE antibodies in the plasma of allergy subjects. In practice, the vaccine can be used against all types of IgE-mediated allergies since the antibodies are not dependent of the antigen specificity of the IgE molecule but will reduce the total IgE pool of the subject. Therefore, the vaccine is aimed at being used for treatment of subjects having different types of IgE-mediated allergies. The increased concentrations of anti-IgE antibodies reduces the free pool of antigen-specific IgE, which thereby strongly reduces the risk for an allergen-mediated release of the physiologically highly active substances which are stored or produced in connection with granula release from mast cells and basophilic leucocytes.

9 Claims, 3 Drawing Sheets

VACCINE COMPRISING PART OF CONSTANT REGION OF IGE FOR TREATMENT OF IGE-MEDIATED ALLERGIC REACTIONS

The present invention relates to a vaccine desired to alleviate the symptoms or prevent the induction of IgE-mediated allergic reactions. Although the invention generally relates to a vaccine for use in a mammal, a preferred embodiment thereof relates to a vaccine for human use and, therefore, the invention will be described below generally with reference to such a vaccine for human use.

BACKGROUND OF THE INVENTION

IgE(immunoglobulin E) is, despite its normally very low concentration in human plasma (10–400 ng/ml), a major cause of hypersensitivities found within the human population. This property is due to its interaction with the high-affinity receptor for IgE on mast cells and basophilic leucocytes.

Cross-linking of two IgE receptors on the surface of these cell types, by allergen binding, initiates the release of a number of physiologically active substances such as histamine, PAF (platelet activating factor), heparin, chemotactic factors for eosinophilic and neutrophilic granulocytes, leucotrienes, prostaglandins and thromboxanes. It is these mediators which cause the direct symptoms of IgE-mediated allergic reactions (Type I hypersensitivity). Disease conditions belonging to this group include most types of asthma, fur allergies, pollen allergies, many types of food allergies and certain types of eczema.

The high-affinity receptor for IgE has been characterized on both protein and gene level in mouse, rat and man (Kinet et al. 1987; Shimizu et al. 1988; Tepler et al. 1989; Blank et al. 1989; Kinet et al. 1989). This receptor probably is present only on mast cells and basophilic leucocytes in our body. The receptor is a complex of three different subunits, the so-called α, β and γ chains. It is the α chain localized mainly extracellularly which interacts with the IgE molecule.

Detailed studies regarding the region of the epsilon chain of the IgE molecule interacting with the high-affinity receptor for IgE have shown that a region of 76 amino acids at the border between the CH2 and CH3 domains (CH=constant domains in the heavy chain) is of decisive importance for the interaction between the IgE molecule and its high-affinity receptor.

This peptide has been shown, in vitro, to be able to inhibit the interaction between native IgE and its high-affinity receptor in a molar ratio of nearly 1:1 compared to the whole CH2-CH3-CH4 region (Helm et al., 1988). The peptide has also been shown to be able to inhibit an IgE-mediated flare reaction in allergen stimulation. However, in this case the concentration is about 10 times the concentration that with native IgE provides the same inhibiting effect (Helm et al., 1989).

When the IgE molecule binds to its receptor, certain regions of the epsilon chain will be blocked for interaction with other molecules, such as e.g. antibodies defected against epitopes within the same region of the IgE molecule. Then, the IgE antibody may only bind to either an IgG antibody directed against the CH2-CH3 region of the IgE molecule or to the receptor and thus never to both of these molecules simultaneously. Antibodies which bind to epitopes outside the region directly interacting with the receptor will, contrary to the ones mentioned previously, give rise to cross-linking of the IgE molecules which are bound to the surface of a mast cell. In this case one will have a very strong release of granula and an anaphylactic shock in the subject in which such an antibody is injected. The antibodies binding to the receptor-bindning portion will, to the contrary, not be able to cross-link these receptors and no immediate reaction arises but an effect of the more prolonged decrease of the concentration of freely circulating IgE. This will probably prevent granula release in that no IgE antibodies are present any longer in the plasma of the subject.

These anti-IgE antibodies will probably also more permanently knock out the IgE-producing B-cell population which increases the possibility to obtain a more long-lasting suppression of the IgE synthesis. During periods of potent pollen exposure, then the antibodies will bind and completely eliminate the pool of IgE which is the cause of the strong inflammatory reaction of pollen-allergic subjects. A number of observations indicate that non-allergic subjects have a relatively high concentration of endogenous anti-IgE antibodies which are believed to have a similar allergy-inhibiting effect.

The effect of the vaccine according to the invention is based on its ability to induce an immune response against the body's own IgE, which, owing to that, will prevent the binding of the IgE antibodies to these receptors. Owing to that, the release of the allergy-inducing substances stored in the mast celles will be prevented.

THE PRIOR ART

A. Receptor-binding peptides and other receptor antagonists

Several research groups throughout the world today work with preparing short peptides or other molecules with the ability to bind to the IgE receptor and thereby prevent binding of antigen-specific IgE. Then, these substances are expected to be able to be used as drugs for the treatment of allergies.

The problem in this case is the great difficulty in obtaining a molecule having a binding strength to the receptor corresponding to the very strong interaction between the native IgE molecule and its receptor. In order to obtain an effective preparation one probably has to work with substances binding irreversibly to the receptor. However, such substances are relatively toxic since they can bind covalently and block other structurally similar molecules in the body. Of interest in this context is that the α chain of the IgE receptor belongs to a larger gene family where i.a. several of the different IgG Fc receptors are contained. These receptors are absolutly essential for the defense of the body against i.a. bacterial infections. Molecules activated for covalent binding are, furthermore, often relatively instable and therefore they probably have to be administered several times a day and then in relatively high concentrations in order to make it possible to block completely the continuously renewing pool of IgE receptors on mast cells and basophilic leukocytes.

B. Anti-IgE monoclonals for allergy treatment

A biotechnology company in USA works according to a model involving production in mice of monoclonal antibodies directed against the IgE receptor-binding region of the human IgE molecule. These antibodies are then "humanised" by genetic engineering in that one replaces the constant regions of the mouse monoclonal with the corresponding human regions. Then, these antibodies are to be prepared in pure form in a large scale in order to be used for injection. The humanisation is used to reduce the immune reaction of the body against said antibodies which otherwise, following the second or third injection, will give rise to a massive immune complex formation which may lead to directly life-threatening complications.

For the treatment of pollen-allergic subjects it will probably be necessary to inject these antibodies once or several times a week during periods of high concentration of pollen. The problem with injection of monoclonal antibodies is that they, even if they are "humanised", will contain high concentrations of new epitopes which the body has never previously been exposed and probably high antibody titers will relatively soon occur even against said monoclonals. This will probably, in the same way as for mouse monoclonals, give rise to life-threatening complications by immune complex formation since the monoclonals still have the "framework"-regions from the murine V-region. In order to avoid these complications it will probably be necessary to use a very large panel of humanised antibodies to be successively alternated during the course of the treatment. Even when administered very accurately they will, however, all the time be followed by the risk of when and to which extent immune complexes will be formed.

C. Peptide vaccines (CH4-ϵ)

A research group led by Dr. Stunworth has worked according to a strategy involving the use of a human peptide coupled to a heterologous carrier protein for immunization in rabbit or rat. In the experiments described by him, they have used the heterologous antiserum from rabbit in order to treat rats. They have not been able to detect any immune response by ELISA in the rabbits in which the antigene has been injected, which shows that the immune response, even with a non-species-specific peptide, is so weak that it is not detectable by one of the most sensitive methods known today (Stanworth et al. 1990). Said group uses short peptides from a region which is clearly outside the receptor-binding (CH2-CH3) portion of the IgE molecule which thereby clearly differs from the present inventive idea which will be disclosed in detail below. A general disadvantage when using short peptides is that they almost completely lack the ability to form a stable secondary structure which probably also is one of the reasons for the very weak immune response in the model system of Dr. Stanworth.

OBJECT OF THE INVENTION

The object of the invention is to provide a vaccine designed to alleviate the symptoms or the induction of IgE-mediated allergic reactions in a mammal, including man, which vaccine induces an immune response against the body's own IgE and thereby will prevent the binding of the IgE antibodies to the IgE receptors, whereby the release of the allergy-inducing substances stored in the mast cells will be prevented.

SUMMARY OF THE INVENTION

The above object is achieved according to the invention by a vaccine which is characterized by containing protein having the entire amino acid sequence of the constant CH2-CH3 domains of the epsilon chain of the IgE molecule from the mammal species in question or a structurally stable unit of said amino acid sequence containing more than 12 amino acids, in its original or in a mutated or multimerized form, the protein optionally being coupled to one or more heterologous carrier proteins, and by optionally containing an adjuvant.

The invention also relates to a process for the preparation of the vaccine and the use of the entire amino acid sequence of the constant CH2-CH3 domains of the epsilon chain of the IgE molecule from a mammal species or a structurally stable unit of said amino acid sequence containing more than 12 amino acids, in its original or in a mutated or multimerized form, for the preparation of a vaccine against IgE-mediated allergic reactions in the mammal species in question.

BRIEF DESCRIPTION OF THE DRAWINGS

In the enclosed drawings the following is shown:

FIGS. 1*a* and 1*b* show the antibody response (the amount of anti-IgE antibodies) in a panel of four different rat strains by ELISA measurement of antibody titers against native rat-IgE and against human IgE (as control).

FIG. 2 shows the suppression of an IgE-mediated inflammatory reaction in a vaccinated rat compared to a blank-immunized rat upon injection of polyclonal anti-IgE antiserum.

DESCRIPTION OF THE INVENTION

The statement that the amino acid sequence (the entire sequence or parts thereof) of the constant CH2-CH3 domains is present in "mutated" form means that amino acids in the sequence may have been mutated by direct exchange or by deletions and insertions, respectively. Then a "slightly" mutated form means that the major part of the amino acid sequence still is the sequence of the protein in its original form and that thereby the effect is almost the same or possibly somewhat reduced in relation to the original sequence; thus, the protein having the "slightly" mutated amino acid sequence is still tolerated by the body and must therefore, similar to its original form, be coupled, according to the invention, to a heterologous carrier protein in order to act as antigen.

By "heavily" mutated form is meant that the exchange, deletion and/or insertion of amino acids involves such interference of the original amino acid seuqence that it functions as antigen by itself since new T-cell epitopes are created by the effected mutation against which the body is not tolerant; in this case it is not necessary to couple the protein to a heterologous carrier protein.

By "multimerized" form is meant that the amino acid sequence (the entire sequence or part thereof) of the protein has been polymerized to a form containing two or more repeating units thereof; by this procedure new T-cell epitopes may be generated at the border between the separate units enabling also this multimerized form of the protein to function as antigen by itself, whereby any coupling to a heterologous carrier protein is not necessary.

The presently preferred embodiment of the invention is the use of a protein having the amino acid sequence (the entire sequence or a part thereof) of the constant CH2-CH3 domains of the epsilon chain of the IgE molecule in its original form, the protein being coupled to one or more heterlogous carrier proteins, and therefore the invention will be described below in detail with reference to this particular embodiment.

The invention is based on an entirely new concept to solve the problems associated with prior art methods for immunization against IgE-mediated allergic reactions in that the vaccine of the invention has the ability to induce an immune response against the body's own IgE.

By triggering the body to produce by itself a polyclonal anti-IgE response antibodies are obtained which are entirely species-specific and owing to that much less immunogenic.

These antibodies will then bind the free pool of IgE circulating in the body and thereby prevent the binding to the IgE receptor. The fact that the immune response is polyclonal and thereby the number of molecules of the same idiotype is very low, will cause the almost complete elimination of the problem of an anti-idiotype response.

The fact that the approach described herein has not been attempted in the prior art is probably to relate to the problem how to obtain a strong IgG response against the body's own IgE, since this is a molecule to which the body has been tolerant since birth and thus does not react against immunologically. In order to solve this problem there is used, according to the invention, a property of the immune system that is scarcely known but which in a uniqe way can solve the problems that, with great probability, will affect the monoclonal projects. By coupling the CH2-CH3 region (the protein) to a non-species-specific protein the tolerance of the immune system to the body's own IgE is circumvented. This leads to the recruitment of a non-tolerized T-cell population which normally would have given rise only to an antibody response against the foreign molecule selected as carrier but which also will give help to B-cells producing antibodies against a species-specific molecule. This effect is obtained by coupling the CH2-CH3 region directly to the carrier protein.

The consequences of this phenomenom has been almost completeley ignored in the immunological community which may explain why no other research group throughout the world has tried a similar approach. The inventor has analyzed in detail the possibility of using this phenomenom, as very few or no similar studies have been performed. In the studies having been made involving coupling of peptides, use has been made of human peptides for injection in rabbit, mouse or rat and not peptides from the same animal species, and the reason for this is the dominating opinion that one cannot produce a strong immune response against species-specific molecules.

In order to confirm that, according to the invention, a strong immune response against a species-specific IgE can be obtained, experiments have been performed where a panel of rat strains has been immunized with a fusion protein containing a carrier molecule coupled to the entire CH2-CH3 domains of the IgE of the rat (Example 2). In these rats there has been obtained (after only 4 weeks) a strong antibody response against native rat-IgE, i.e. the form of IgE circulating in the plasma of the rat. This antibody response has a strength that is only insignificantly lower than the level (of the antibody response) that in ELISA measurements is obtained against a completely non-species-specific protein, in this case human IgG (FIG. 1).

The reason why the inventor, in contrast to Dr. Stanworth, obtains such a strong immune response is probably because the invention uses larger regions than peptides having only a length of about 10 amino acids, i.e. in this case up to the entire CH2-CH3 domains. This is the reason why a much greater number of epitopes, against which antibodies can be formed, is obtained and further that these epitopes are in the same conformation as in the native IgE molecule.

By "heterologous carrier protein" is meant herein any non-species-specific protein which rather does not possess too high homology to the corresponding protein of the species in which the protein is to be used as carrier. However, such proteins should be avoided which normally are not in our surroundings since a very strong immune reaction may cause problems if we often are exposed to this protein.

By coupling small peptides to a heterlogous carrier protein, normally only a relatively weak immune response is obtained against a very restricted region of the molecule. Further, peptides to a very large extent give rise to an immune response that only reacts against the peptide and not against the corresponding region of the native protein.

It is important to obtain a very strong immune response which, furthermore, recognizes native IgE, since the binding constant for the interaction between the IgE molecule and the high-affinity receptor is very high and is within the range of from $1 \times 10^{-8}$ to $2.6 \times 10^{-10}$ or higher (Froese, 1980). By obtaining, after immunization, a polyclonal response several different antibodies directed against different epitopes within the CH2-CH3 region will be able to bind simultaneously to the same IgE antibody. This provides for the obtaining of a very high combined binding strength for free IgE. Thereby the anti-IgE antibodies considerably easier, compared to the case of a monoclonal antibody or of antibodies formed against short peptides, will be able to compete for free IgE of the immunized subject. This of great importance since the interaction between the IgE and the high-affinity receptor is very strong. The inventive idea of using entire domains or strutrurally stable parts thereof therefore involves a very great advantage and an entirely new concept compared to the peptide approaches previously described.

The antibody response against peptides often has a low or no affinity for the corresponding amino acid region of the native protein which means that the antibody response obtained against entire domains or structurally stable units of domains brings about a decisive difference compared to previous approaches in the art.

Figure 2:
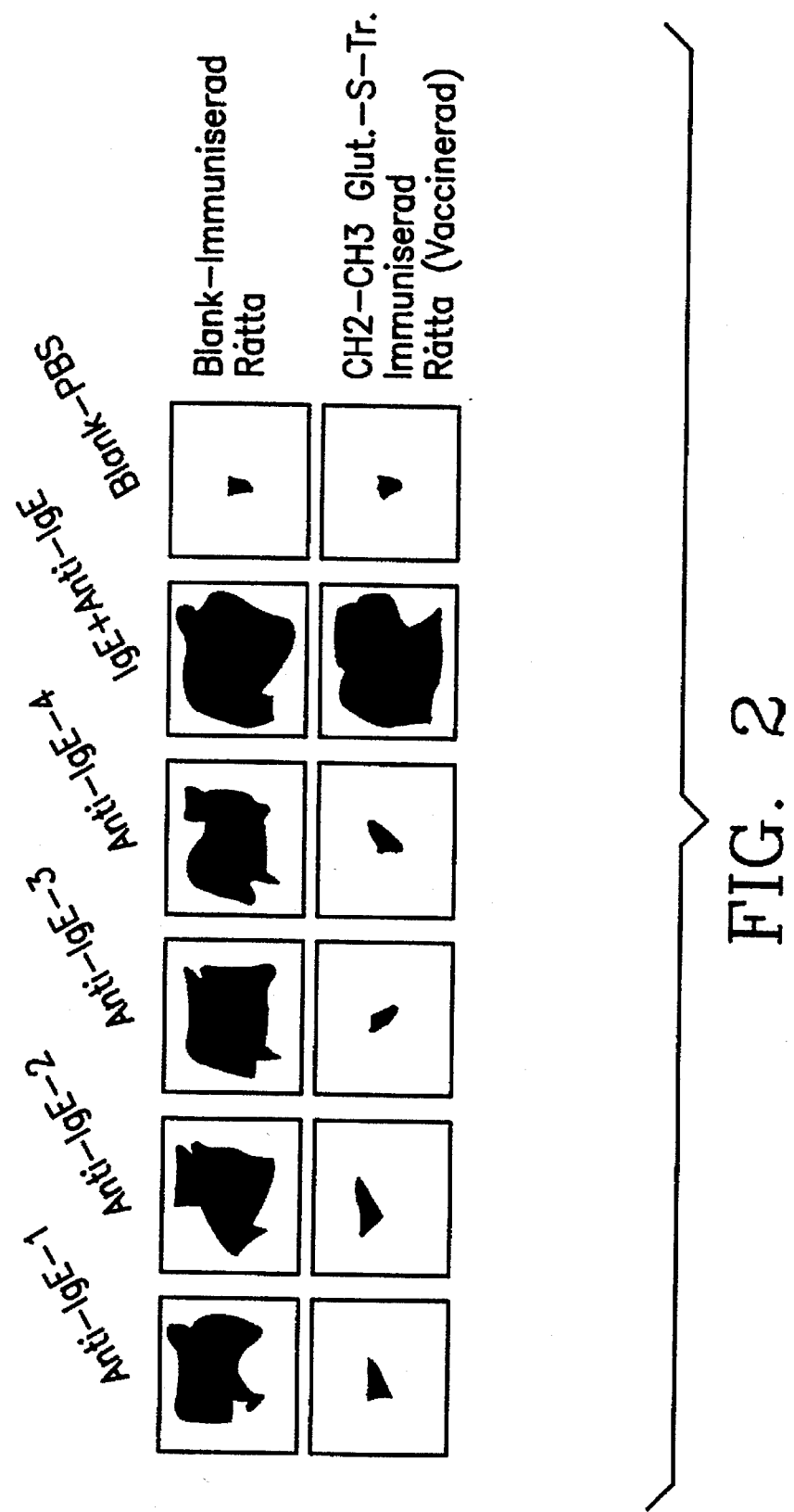

By using only the CH2-CH3 region (and not, as earlier described, heterologous CH4 peptides) of the IgE molecule, the body, after immunization, will almost exclusively form antibodies against the region of the IgE molecule interacting with the IgE receptor. In theory, there is a risk that antibodies directed against the N-terminal part of the CH2 domain or the C-terminal part of the CH3 domain may give rise to an anaphylactic shock in the mammals in which these antibodies are formed. However, the variable region of the antibody corresponds to the size of an entire domain and therefore, in most cases, steric hindrance for receptor binding will be obtained even with such antibodies. In addition, the antibodies will be produced continuously against a great number of epitopes while the immune response builds up and therefore the probability that only one of these very few antibodies alone shall bind an IgE molecule is probably very low. However, a number of animal tests has shown that such effects of the immunization cannot be detected (cf. Example 2 below). The rats having high contents of anti-CH2-CH3 antibodies in their blood do not show any tendency to symptoms of any anaphylactic shock. From the view point of health they cannot be differentiated from animals having been immunized solely with adjuvant (with no antigen) or from animals having been immunized with human IgG. This indicates that in test animals there are no detectable negative effects of this immunization even if the animals have very high anti-IgE titers. Thereby it is the first time that it has been shown that one can obtain high anti-IgE titers against species-specific IgE. Further, these rats do not show any detectable negative effects of these treatment indicating that the treatment procedure with great probability can also be used, with no complications, to treat humans. Furthermore, these data strongly indicates that the IgE receptor-bound IgE pool in these rats is virtually non-existent. Otherwise, a strong anaphylactic reaction of the anti-IgE antibodies that are able to bind to the previously mentioned outer regions of the CH2 and CH3 domains should be induced, even if the antibody titer is relatively low for such antibodies. This is because the mast cells are very sensitive even to very low concentrations of cross-linking antibodies. In preliminary studies it has been shown that, upon immunization, the animals in which high anti-IgE titers occur have a very strongly reduced tendency to release their mast cell granula following provocation with anti-IgE antibodies (Example 3; FIG. 2). The inventor is currently performing a much larger study involving the treatment of rats which have been made strongly allergic against hen ovalbumin. The results from the tests on rats so far performed are very promising from several aspects, because they show that a strong immun response is obtained which has no detectable negative effects and finally that a strongly reduced granula release is obtained upon addition of a polyclonal activator in these rats.

A vaccine of this type may be faced with certain difficulties. One factor strongly affecting the possibilities is the concentration of the substance which it is desirable to remove from the body. High concentrations in this case mean greater difficulties. If in this context any of the other immunoglobulin isotypes had been selected, the problem should have been even greater because of the generally much higher plasma concentrations of these antibodies.

Because of its low plasma levels in this context IgE is ideal. The plasma levels in a normal population of non-allergic subjects are from 10 to 400 ng/ml. This amount corresponds to less than 0.01% of the total immunoglobulin amount in our blood. These levels are often somewhat increased in allergic subjects but very seldom exceeds 5 µg/ml. As a comparison some tests performed in mouse can be mentioned here where, by using antibodies directed against one of the light chains of the immunoglobulins, animals have been obtained which almost completely lack this type of immunglobulins. In these tests, by injecting monoclonal antibodies against the k-chain of the immunglobulin of the mouse, corresponding to about 95% of the total immunoglobulin amount of the mouse, an almost complete loss of these antibodies in the blood of the mouse has been obtained (Weiss et al., 1984). The remaining antibodies found in the mouse are, to almost 100%, of the Ig λ type (the original concentration of Ig λ is only about 5%). This shows that, even in case of considerably higher concentrations of the substance to be removed from the body, there is a possibility to remove almost completely said substances from the circulation.

Another possible complication is that nothing is known about the long-term effects of inducing a strong autoimmunity. However, an advantage is that in this case T-cells are used directed against non-species-specific molecules in order to generate an immune response against a species-specific antigen. If the vaccination program is terminated, the antibody response against the body's own IgE will slowly decrease to non-detectable levels after some month. This occurs if one does not booster with CH2-CH3 coupled to the very same carrier molecule that is used in the initial vaccination. This phenomenom has been shown in many detailed studies in mouse, where it has been shown that the secondary immune response against haptens, coupled to different carriers, is entirely dependent on the carrier molecule initially selected. If any subject for some improbable non-foreseeable reason would react negatively to this immunization, the immunization can be terminated and the antibody titers will probably reach non-detectable levels within a few months. This is similar to what would be the case when injecting monoclonal antibodies directed against the body's own IgE.

The coupled protein used as major component of the anti-allergy vaccine can, from a technical point of view, be prepared in two different ways. One involves the production of an already coupled protein, a so-called fusion protein, in procaryotic or eucaryotic host cells. As procaryotic hosts normally the bacterium *Escherichia coli* is used, while a number of different systems such as yeast cells or cell lines can be used as eucaryotic hosts. The cell lines may be derived from insects to human beings. However, human cells are normally avoided for clinical use since there is always a risk of contamination by human virus in the cell cultures. The second technique is based on a direct chemical coupling of the carrier protein and the active species-specific component, in this case the entire or part of the CH2-CH3 region of the IgE molecule. Then, the proteins are produced separately. This technique is the one normally used in immunizations with synthetic peptides as well as in immunization with small haptens (of substances which are not proteins) and is based on chemical activation of the carrier protein with e.g. CNBr and then mixing of the activated carrier with the peptide or the protein fragment which one wishes to couple together. These two are then coupled covalently to each other.

The immunization is performed by mixing soluble or aggregated protein vaccine with an immune response potentiating substance (adjuvant) which is then injected subcutaneously, intraperitoneally or intramuscularly. The rats so far studied have been injected with the vaccine subcutaneously or intraperitoneally. In these tests use has been made of amounts of about 100 µg of antigen per rat and immunization occasion and with these concentrations very strong immune responses have been obtained in a panel of different rat strains (FIG. 1). In humans there will be used in the first place relatively weak non-toxic adjuvants, such as Alum, or, as an alternative, injections of larger amounts of aggregated fusion protein with no addition of adjuvant. The aggregated fusion protein is intended to increase the immunogenicity of the protein.

Further, in humans probably considerably larger amounts of the antigen will be used, possibly in the order of 100–500 mg of pure protein. From a technical point of view this does not involve any greater problems since it is possible to obtain very large amounts of this fusion protein in a very pure form and to a price which is not too deterrent. In the present situation there are a number of fusion protein variants in small-scale production for the human vaccine as well as for the rat vaccine. However, the analysis of the human vaccine waits for the results from the very large study which is presently being undertaken in different rat strains.

Repeated injections are initially made with about 3 weeks interval in order to obtain a strong immune response. Thereafter, it will probably be necessary to perform the immunizations only a few weeks prior to each pollen period for a pollen-allergic subject, in order to activate the previous immune response and strongly amplify this response before the new high-risk period.

Further, by using a number of heterologous carrier molecules, to which species-specific proteins or protein fragments have been coupled, the percentage number of T-cells will increase. These will give help to B-cells which produce antibodies directed against, as in this case, the CH2-CH3 region of the human IgE molecule. By this refinement of the immunization protocol one expects to be able to decrease the amounts of antigen that need to be used for the immunization while retaining the immunization effect. This latter approach will not be of immediate interest until when clinical tests in humans are performed, where strong adjuvants cannot be used and therefore all available methods must be used in order to increase the immunogenicity of the vaccine.

As mentioned above, the purpose of the invention is primarily to prepare vaccine for use in humans. However, within the scope of the invention are also vaccines for other mammal species where there is economically important to vaccinate against IgE-mediated allergic reactions. Example of such species are dogs, horses and pigs.

The invention will be illustrated further below by the following specific working examples.

EXAMPLE 1

Production of a Fusion Protein Preparation of the CH2-CH3 Region of the Epsilon Chain of IgE from Humans and Rat In this Example use has been made of a system where the species-specific protein and the carrier protein are produced in bacteria, in this case *Escerichia coli*, in a coupled form. By means of PCR technique (Polymeruse Chain Reaction) the cDNA sequences for the CH2-CH3 regions of both the human and the rat epsilon chain of IgE have been cloned and ligated into a commercially available vector for the production of a fusion protein in bacterial hosts. The vector used is a member of the so-called pGEX vectors of form 1, 2 or 3 with different reading flames for ligation of cDNA fragments (Smith and Johnson, 1988). This type of vectors has, in this case, been shown to give high yields of pure fusion protein for direct immunization. In this vector family the entire coding region for a 26 kD glutathione-S-transferase (Sj26) from the parasitic worm *Schistosoma japoncium* is cloned-in after a strong and inducible bacterial promotor. This promotor, a so-called tac-promotor, is negatively regulated by the lac-repressor. To obtain large amounts of protein, inhibition of the promotor is releaved by means of IPTG (isopropyl-$\beta$-D-thiogalactoside). Following ligation of the CH2-CH3 fragment into the vector in the C-terminal part of the Sj26 gene, this vector is transformed into a *E. coli* strain for the production of the fusion protein. An overnight culture of this new bacterium, containing the vector into which the desired fragment has been ligated, is diluted in the ratio 1:10 in bacterial growth medium and is allowed to grow further for 2 hours. Then IPTG is added to 100 $\mu$M and the culture is incubated during vigorous shaking for 4 further hours. Then, the bacteria are harvested by centrifugation and the cell pellet is washed 3 times in PBS. Following washing the cells are suspended in PBS+1% Triton X-100 och are sonicated for 5×15 seconds in order to break the cell walls of the bacteria to release the protein from the cells. It has been shown that in case of both the rat and the human CH2-CH3 fusion proteins, the protein precipitates intracellularly as crystals and therefore has to be solubilized by means of a solution containing 8M urea. Then, the human protein can be dialysed against pure PBS and become completely soluble. At present there is work going on to obtain a protocol for large-scale purification to a purity of almost 100% for the human fusion protein. However, the CH2-CH3 fusion protein of the rat is more insoluble and most of the protein precipitates already after dialysis for half an hour to an hour. In the following Examples use has been made of a fusion protein preparation of the rat CH2-CH3 having a purity of about 50%. These preparations have been used to study the possibility of obtaining a strong antibody response against the rat's own IgE and to study the possibilities of blocking a strong IgE-mediated inflammatory reaction in rat. The remaining 50% of the protein in the preparation consists of different contaminating bacterial proteins, whereby a single protein is no more than 10% of the total protein.

EXAMPLE 2

Immunization of Rat—Measurement of Immune Response

Immunization or vaccination is performed by means of the fusion protein preparation from Example 1 in admixture with an immune response potentiating substance (adjuvant) to form a vaccine. The rats having been studied have been injected with the vaccine subcutaneously or intraperitoneally with a mixture of soluble and aggregated protein. In these tests use has been made of amounts of about 100 $\mu$g of antigen per rat in 0.2 ml of Freund's complete adjuvant and incomplete adjuvant, respectively, per immunization occasion and rat. With these concentrations and adjuvants very strong immune responses have been obtained in a panel of different rat strains.

In FIGS. 1a and b there is shown a test with four different rat strains and three rats per strain. The antibody titers against native IgE have been measured by means of ELISA. This assay has been performed in such a way that native IgE in coating buffer (5 $\mu$g/ml) has been used for coating of the ELISA plates. Successive dilutions (⅕) of rat serum from the different test animals have then been tested for colour reaction in the ELISA. The absorbance values at 400 nm are depicted on the Y-axes in FIG. 1 and the different ⅕ dilutions, with increasing dilutions to the right in the Figure, are depicted on the X-axes.

The four different rat strains (Lewis, Sprague Dawley, Wistar and Brown Norway) have been analyzed, in the left panel, for their ability to respond to the CH2-CH3 vaccine and, in the right panel, against human IgG (as control). The vaccine used is the CH2-CH3 of the rat, which in the rat entirely corresponds to the human vaccine. These rats have only been vaccinated twice; to begin with one vaccination with Freund's complete adjuvant and protein solution and then a second vaccination three weeks later with the same protein solution in Freund's incomplete adjuvant. One week after the second vaccination blood samples were taken from the rats. The content of anti-IgE antibodies in the blood was then determined by ELISA assay. As can be seen clearly from the Figure, three of the strains respond very well to the vaccine while the fourth strain is a so-called "nonresponder" which is not so unusual when using, as in this case, congenic strains. By this is meant that this very rat strain cannot present this antigen for the immune system and that, therefore, it would be necessary to use another heterologous carrier protein in this rat strain in order to obtain the desired effect of the allergy vaccine.

As can be seen from these initial ELISA measurements a very strong immune response is obtained against only two domains of the rat IgE, which has to be compared with the only slightly stronger reaction obtained against the human IgG which, in addition, has a size corresponding to four domains. These rats, showing very high anti-IgE titers, do not show any negative symptoms whatsoever. In practice they cannot, by any criteria, be distinguished from the rats having been immunized only with pure PBS in Freund's adjuvant (the controls, marked "blank" in FIG. 1).

EXAMPLE 3

Immunization of Rat—Suppression of an IgE-mediated Inflammatory Reaction

Studies aimed at assessing the ability of the vaccine of the invention to suppress a strong IgE-mediated inflammatory reaction have also been performed. As an assay system use has been made of the fact that anti-IgE antibodies have an ability to cross-link IgE antibodies bound to mast cells of the skin and to induce, by their ability to cross-link these IgE molecules, a potent granula release and thereby provoke a strong inflammatory reaction on the place there the antibodies have been injected (in this case the skin). In this example use has been made of a polyclonal anti-IgE antiserum directed against the entire constant region of IgE. Therefore, this serum should contain large amounts of cross-linking antibodies which is also confirmed by the results. The strength of the inflammation is then measured by means of a colour reaction. The permeability and accordingly the leakage from the blood of different blood proteins increased strongly in the region where the inflammation has been provoked. The stronger the inflammation is, the larger blue zone is obtained if one injects a 1% Evans Blue solution into the blood of the test rats two hours before reading the size of the blue zone underneath the skin of the test animals. The test, which is shown schematically in FIG. 2, was performed in such a way that four injections of each 50 µl of a concentrated solution of a polyclonal anti-IgE antiserum were made under the skin of a vaccinated rat and a blank-immunized rat two hours before removal of the skin and measurement of the inflammation zones. As control injections were made of IgE+anti-IgE on one spot per rat and of only PBS on one spot. Two typical examples of these rats are shown in the Figure, where one of the rats was immunized with CH2-CH3 vaccine in Freund's adjuvant and the other control rat was immunized with PBS in Freund's adjuvant. The zones of the IgE+anti-IgE controls have a very similar size for the two rats, whereas the zones for injections with only anti-IgE antibodies have been reduced to nearly zero for the vaccinated rat. Anti-IgE antibodies solely invoked strong blue zones for the blank-immunized rat (as control). This shows that the vaccinated rat probably completely lacks IgE antibodies on the surface of its mast cells, which is in complete agreement with the result to be expected from the immunizations, where in these rats high concentrations of endogenous anti-IgE antibodies have been found. However, they do not lack mast cells since it is possible to retain a normal blue zone by adding exogenous IgE together with the anti-IgE antibodies and thereby again bind the mast cell receptors onto these mast cells which probably originally were free from IgE.

At present work is performed with very promising results in a new rat model where, to begin with, a very strong IgE response is invoked in Wistar rats which respond well to the rat vaccine according to the invention (cf. FIG. 1). Immunization of the rats is performed with a specific antigen which in this case is ovalbumin together with the toxin Ricin, according to a newly developed protocol by Dr. Kemeny (Diaz-Sanchez and Kemeny, 1991). After a number of weeks these rats obtain a very strong IgE response to ovalbumin and, furthermore, this immune response is relatively long-lasting. Initial studies have given very good results with this protocol. A number of rats has been analyzed for their ability to give rise to a strong inflammatory reaction in the skin after injection of 50 µl of a solution containing 5 mg/ml of ovalbumin. This has given blue zones which are nearly twice as large as the previously mentioned positive controls with IgE+anti-IgE, which shows that these rats are extremely allergic to ovalbumin. This type of rats are today used to study the possibility of blocking allergy reactions in the skin and then to study the effects on bronchocontrictions and other typical allergy-related symptoms.

Below will follow, in four points, a summary of the essential differences between the present invention and the prior art.

1. The invention focuses solely on the domains of the IgE molecule which are directly involved in the interaction with the IgE receptor and not, as in previous studies, on regions in the non-receptor-interacting C4-domain.

2. The vaccine of the invention contains species-specific protein fragments, coupled to one or more heterologous carriers, which makes it possible to mount a strong autoimmune response, in contrast to earlier studies, where use has been made of epsilon peptides from another species than the one in which the coupled peptide is injected, i.e. human peptides in mouse, rat or rabbit.

3. Contrary to the monoclonal projects going on in several laboratories throughout the world the invention is based upon the generation of a polyclonal immune response to a species-specific protein, which considerably increases the possibilities to obtain a successful result since thereby immune complex-related complications, leading to life-threatening inflammatory reactions, will most probably be avoided.

4. The most important difference is that, according to the invention, use is made of entire domains or structurally stable parts thereof (having more than 12 amino acids) as vaccine. Thereby there is obtained a strong polyclonal response in test animal systems (already shown) against native IgE, which is a very important property of a vaccine of this type (also shown). This is obtained after only a few weeks immunization, which means a very great progress compared to the previous approaches made in the art with short synthetic peptides.

References:

Blank U., Miller R., White K., Metzger H. and Kinet J.; Complete structure and expression in transfected cells of high affinity IgE receptor. Nature 337 (1989) 187–189.

Froese A. CRC crit. Rev. Immunol. 1. (1980) 79–132.

Helm B., Marsh P., Vercelli D., Padlan E., Gould H. and Geha R.; The mast cell binding site on human immunoglobulin E. Nature 331 (1988) 180–183.

Helm B., Kebo D., Vercelli D., Glovsky M., Gould H., Ishizaka K., Geha R. and Ishizaka T.; Blocking of passive sensitization of human mast cells and basophil granulocytes with IgE antibodies by a recombinant human ε-chain fragment of 76 amino acids. Proc. Natl. Acad. Sci. USA. 86 (1989) 9465–9469.

Kinet J., Metzger H., Hakimi J. and Kochan J.; A cDNA presumtively coding for the α subunit of the receptor with high affinity for immunoglobulin E. Biochemistry 26 (1987) 4605–4610.

Kinet J., Blank U., Ra C., White K., Metzger H. Kochan J.; Isolation and characterization of cDNAs coding for the β subunit of the high-affinity receptor for immunoglobulin E. Proc. Natl. Acad. Sci. USA. 85 (1988) 6483–6487.

Stadler B., Nakajima K., Yang X., and Weck A.; Potential role of anti-IgE antibodies in vivo. Int. Arch. Allergy Applied Immunol. 88 (1989) 206–208.

Shimizu A., Tepler I., Benfey P., Berenstein E., Siraganian R. and Leder O.; Human and rat mast cell high-affinity immunoglobulin E receptors: Characterization of putative α-chain gene products. Proc. Natl. Acad. Sci. USA 85 (1988) 1907–1911.

Stanworth, D. R. Jones, V. M., Lewin, I. V. and Nayvar, S.; Allergy treatment with a peptide vaccin. The Lancet 336 (1990) 1279–1281.

Tepler I., Shimizu A. and Leder P.; The gene for the rat mast cell high affinity IgE receptor α chain. J. Biol. Chem. 264 (1989) 5912–5915.

WEISS S:; Lehmann K., Raschke W. C., and Cohn M.; Mice completely suppressed for the expression of immunoglobulin k light chain. Proc. Natl. Acad. Sci. USA. 81 (1984) 211–215.

Vercelli D., Helm B., Marsh P., Padlan E., Geha R. and Gould H.; The B-cell binding site on human immunoglobulin E. Nature 338 (1989) 649–651.

Smith, D. B. and Johnson, K. S. Single-step purification of polypeptides expressed in *Escherichia coli* as fusion with glutathion S-transferase. Gene 67 (1988) 31–40.

Diaz-Sanchez, D. and Kemeny, D. M. Generation of long-lived IgE response in high and low responder strains of rat by co-administration of ricin and antigen. Immunology 72 (1991) 297–303.

I claim:

1. A method of immunization of a mammal against IgE-mediated allergic reactions, which comprises injecting into the mammal an immunogen comprising a carrier protein that is foreign to the mammal and to which is coupled a fragment of the epsilon chain of the IgE consisting of the CH2CH3-domains thereby enabling said mammal to produce, after having received said immunogen through injection, polyclonal antibodies to native IgE which antibodies are able to bind to circulating native IgE.

2. The method according to claim 1, wherein the injection is made preceding a period of high potential for an allergy reaction in the mammal.

3. The method of claim 1, wherein the immunogen is a fusion protein between the carrier protein and the entire CH2CH3 domain of the epsilon chain of IgE.

4. A method of immunization of a mammal against IgE-mediated allergic reactions, which comprises injecting into the mammal an immunogen comprising a carrier protein that is foreign to the mammal and to which is coupled a fragment of the epsilon chain of the IgE consisting of the CH2CH3-domains being in a multimerized form so that said mammal, after having received said immunogen by injection, produces polyclonal antibodies which are able to bind to circulating native IgE.

5. The method according to claim 4, wherein the injections are made preceding a period of high potential for an allergy reaction in the mammal.

6. A vaccine comprising as the immunogen a carrier protein that is foreign to the mammal and to which is coupled a fragment of the epsilon chain of the IgE consisting of the CH2CH3-domains thereby enabling said mammal to produce, after having received said immunogen through injection, polyclonal antibodies to native IgE which antibodies are able to bind to circulating native IgE.

7. A vaccine according to claim 6, wherein the immunogen is a fusion protein consisting of said CH2CH3-domains fused with said carrier protein.

8. A method of immunization of a mammal against IgE-mediated allergic reactions, which comprises injecting into the mammal an immunogen comprising a carrier protein that is foreign to the mammal and to which is coupled a fragment of the epsilon chain of the IgE consisting of the CH2CH-domains so that said immunogen has sufficient epitopes in the same conformation as in the native IgE molecule thereby enabling said mammal to produce, after having received said immunogen through injection, polyclonal antibodies to native IgE which antibodies are able to bind to circulating native IgE.

9. A vaccine comprising as the immunogen a carrier protein that is foreign to the mammal and to which is coupled a fragment of the epsilon chain of the IgE consisting of the CH2CH3 domains so that said immunogen has sufficient epitopes in the same conformation as in the native IgE molecule thereby enabling said mammal to produce, after having received said immunogen through injection, polyclonal antibodies to native IgE which antibodies are able to bind to circulating native IgE.

* * * * *